US006782072B2

(12) United States Patent
Lin

(10) Patent No.: US 6,782,072 B2
(45) Date of Patent: Aug. 24, 2004

(54) METHOD OF ANALYZING COMPOSITION DEPTH PROFILE OF SOLID SURFACE LAYER

(75) Inventor: Liu guo Lin, Tokyo (JP)

(73) Assignee: Oki Electric Industry Co., Ltd., Tokyo (JP)

(*) Notice: Subject to any disclaimer, the term of this patent is extended or adjusted under 35 U.S.C. 154(b) by 0 days.

(21) Appl. No.: 10/421,851

(22) Filed: Apr. 24, 2003

(65) Prior Publication Data

US 2004/0071270 A1 Apr. 15, 2004

(30) Foreign Application Priority Data

Oct. 9, 2002 (JP) .................................. 2002-295593

(51) Int. Cl.⁷ .............................................. G01N 23/22
(52) U.S. Cl. ............................... 378/45; 378/44; 378/48
(58) Field of Search .............................. 378/44, 45, 48

(56) References Cited

U.S. PATENT DOCUMENTS

| 4,518,678 A | | 5/1985 | Allen |
| 5,028,778 A | * | 7/1991 | Ninomiya et al. .......... 250/305 |
| 6,395,610 B1 | | 5/2002 | Roy et al. |
| 2003/0155501 A1 | * | 8/2003 | Parker et al. ............... 250/282 |

FOREIGN PATENT DOCUMENTS

| JP | 06-222019 | 8/1994 |
| JP | 11-204787 | 7/1999 |

OTHER PUBLICATIONS

Kozo Tanaka et al., "Xray photoelectron spectorscopy", Maruzen Co., Ltd., pp., 222–225.

G–L. Liu et al. "The Analysis of Nitrogen Profiles in Ultra–thin SiON film by using AR–XPS", The Japan Society of Applied Physics and Related Societies, No. 2, Mar. 27, 2002 (28a–A–4).

Rama I. Hedge et al., "Growth and Film Characteristics of N2O and NO Oxynitride Gate and Tunnel Dielectrics", J. Electrochem. Soc., vol. 144, No. 3, Mar. 1997, pp. 1081–1086.

M. Pijolat et al., "New Depth–Profiling Method By Angular–Dependent X–Ray Photoelectron Spectroscopy", Surface Science 105 (1981) pp. 114–128.

* cited by examiner

Primary Examiner—David V Bruce
(74) Attorney, Agent, or Firm—Volentine Francos, PLLC

(57) ABSTRACT

A method of analyzing a composition depth profile of a solid surface layer, wherein actually-measured intensity of photoelectrons emitted from the solid surface layer by irradiating the solid surface layer containing at least two or more species of element with X rays and photoelectron calculated intensity obtained by making a calculation assuming an elemental composition ratio for each of a plurality of sub-layers into which the solid surface layer has been temporarily divided are utilized to determine a composition depth profile of the solid surface layer, the method including a step of at least repeating an approximate calculation including: distinguishing a specified sub-layer such that the calculated intensity best converges to the actually-measured intensity in the sub-layers; and correcting an elemental composition ratio at least for the specified sub-layer so that the calculated intensity converges to the actually-measured intensity, thereby determining the composition depth profile of the solid surface layer.

14 Claims, 4 Drawing Sheets

METHOD OF ANALYZING COMPOSITION DEPTH PROFILE OF SOLID SURFACE LAYER

BACKGROUND OF THE INVENTION

1. Field of the Invention

The present invention relates to a method of analyzing a composition depth profile of a solid surface layer using X rays. The method is especially suitable for an evaluation of composition depth profiles of gate insulating films of transistors (Tr), which are used as portions of semiconductor integrated circuits.

2. Description of Related Art

As semiconductor devices (Large Scale Integrated Circuit, LSI) become finer, ultrathin nitride-oxide films (1 nm to a few nm) are beginning to be introduced as gate insulating films of transistor cells. Functions of gate insulating films depend to a large degree on densities and distributions of nitrogen (N) in the nitride-oxide films. Therefore, film qualities of such nitride-oxide films have been studied using the secondary ion mass spectrometry (SIMS) and the X ray photoelectron spectroscopy (XPS) in recent years (for example, see R. I. Hedge, B. Maiti, and P. J. Tobin: J. Electrochem. Soc., Vol. 144, No. 3, March 1977, pp. 1081–1086).

SIMS is a technique characterized by including steps of causing primary ions to impinge on a sample to sputter it, and analyzing in mass and detecting the sputtered secondary ions. In the case where a nitride-oxide film as described above, wherein N is distributed in a very shallow region in the film, is analyzed using SIMS, the following effects will arise: the mixing effect of the primary ions (an effect such that the primary ions incident on a sample mix the target elements to be detected and the matrix elements of the sample in a region up to a certain depth from the surface thereof); and the knock-on effect (an effect such that an impact energy of primary ions cause the target elements to be forced to the direction of the depth).

In the case of using SIMS to analyze nitride-oxide films, the mixing effect and the knock-on effect make a detected density of nitrogen lower than the actual density and diffuse nitrogen atoms in the sample around the measured region to spread the distribution of the nitrogen atoms in analyzing it. As a result, the density and distribution of N with respect to the direction of the film thickness can not be measured accurately.

In contrast, XPS is an analyzing technique characterized by steps of irradiating a sample with X rays, and spectroscopically analyzing the excited photoelectrons to determine the intensities of detected elements. Especially, the angle-resolved XPS is used to measure the distributions of elements in a thin film (for example, see (1) M. Pijolat and G. Hollinger, Surface Science 105, 1981, pp. 114–128, and (2) Ryu, et al., Dai 49-kai Ouyo-busuri Kankei-rengo Koenkai (49th lecture meeting of applied physics-related alliance), the collection of preliminary reports of the lectures p.815). The evaluation of the density distributions of elements in the direction of the film thickness using the angle-resolved XPS utilizes a principle such that the intensities of photoelectrons created at a depth (x) below the sample surface are exponentially attenuated according to the relation shown by the following equation (1) when the photoelectrons reach the sample surface.

$$I(x) = I_0(x)\exp\left(\frac{-x}{\lambda\sin\theta}\right) \quad (1)$$

where x is a depth below the sample surface (solid surface), $\lambda$ represents an inelastic scattering mean free path of photoelectron, $\theta$ represents an angle which the sample surface forms with the detector and X rays, $I_0$ represents an intensity of photoelectrons created at a depth x below the sample surface, and $I_x$ represents an intensity of photoelectrons created at a depth x when the photoelectrons reach the sample surface. As shown in Equation (1), when making the angle $\theta$ smaller, the path which photoelectrons created in the sample travel along to reach the sample surface becomes longer to increase the attenuation in photoelectron intensity. On the other hand, when making the angle $\theta$ larger, the path becomes shorter and thus the attenuation in photoelectron intensity becomes smaller.

More specifically, the density distributions of elements in the direction of the film thickness have been determined by the angle-resolved XPS including the steps of: assuming density distributions of target elements to be detected in the film; calculating the detected intensities of the elements when the sample is irradiated with X rays at a variety of angles $\theta$; and repeating the step of assuming the density distributions of the elements until the photoelectron intensities calculated by the least squares method converge to the actually-measured photoelectron intensities.

However, the conventional method using the angle-resolved XPS has no selectivity to cause calculated intensities of photoelectrons to converge to the actually-measured intensities effectively and efficiently and thus the method has required much time to conduct the calculation to determine a composition depth profile of a solid surface layer.

The invention was made to solve the above-described problem. In other words, it is an object of the invention to provide a method of analyzing a composition depth profile of a solid surface layer, which enables us to determine the density distributions of elements in a solid surface layer in the direction of the film thickness simply and accurately for a short time. The method is realized by the addition of selectivity to cause photoelectron calculated intensities to converge to the actually-measured intensities effectively and efficiently.

SUMMARY OF THE INVENTION

The invention can solve the above problems. In other words, the invention provides a method of analyzing a composition depth profile of a solid surface layer, wherein actually-measured intensities of photoelectrons emitted from the solid surface layer by irradiating the solid surface layer containing at least two or more species of elements with X rays and photoelectron calculated intensities obtained by making a calculation assuming an elemental composition ratio for each of a plurality of sub-layers into which the solid surface layer has been temporarily divided are utilized to determine the composition depth profile of the solid surface layer. The method of the invention includes the step of at least repeating an approximate calculation including: distinguishing a specified sub-layer such that the calculated intensities best converge to the actually-measured intensities in the sub-layers; and correcting elemental composition ratios at least for the specified sub-layer so that the calculated intensities converge to the actually-measured intensities, thereby determining the composition depth profile of the solid surface layer.

DETAILED DESCRIPTION OF THE INVENTION

Figure 1:
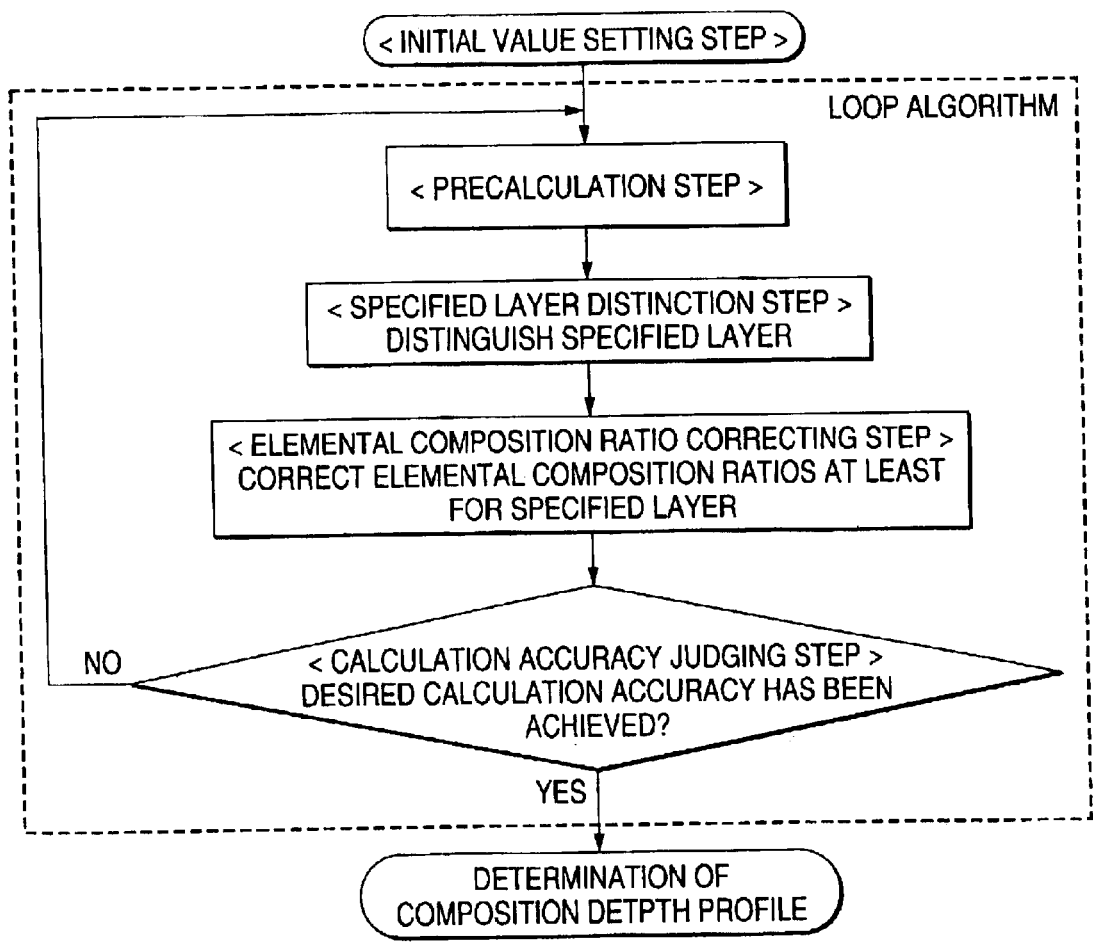
FIG. 1 is a flow chart showing an embodiment of a method of analyzing a composition depth profile of a solid surface layer according to the invention.

A method of analyzing a depth profile of a solid surface layer according to the invention will be described below.

The invention provides a method of analyzing a composition depth profile of a solid surface layer, characterized in that actually-measured intensities of photoelectrons emitted from the solid surface layer by irradiating the solid surface layer containing at least two or more species of elements with X rays and photoelectron calculated intensities obtained by making a calculation assuming an elemental composition ratio for each of a plurality of sub-layers into which the solid surface layer has been temporarily divided are utilized to determine the composition depth profile of the solid surface layer. The method of the invention is further characterized by including the step of at least repeating an approximate calculation including: distinguishing a specified sub-layer such that the calculated intensities best converge to the actually-measured intensities in the sub-layers; and correcting elemental composition ratios at least for the specified sub-layer so that the calculated intensities converge to the actually-measured intensities, thereby determining the composition depth profile of the solid surface layer.

As described above, the invention includes the step of repeating a selective approximate calculation, which includes: distinguishing a specified sub-layer such that calculated intensities converge best to the actually-measured intensities and correcting elemental composition ratios at least for the specified sub-layer so that calculated intensities converge to the actually-measured intensities. Therefore, the invention allows the simple and accurate determination of density distributions of the elements in a solid surface layer in the direction of the film thickness for a short time.

Incidentally, a conventional method, by contrast, utilizes the least squares method to correct elemental composition ratios for all sub-layers, into which a solid surface layer has been temporarily divided, so that calculated intensities converge to the actually-measured intensities. Thus, the conventional method requires a lot of time.

The invention requires correcting elemental composition ratios at least for the specified sub-layer when correcting the elemental composition ratios so that calculated intensities converge to the actually-measured intensities. However, the phrase "elemental composition ratios at least for the specified sub-layer" in this case concretely represents elemental composition ratios of the specified sub-layer and the sub-layers in the vicinity of the specified sub-layer.

Further, in the case where a solid surface layer is temporarily divided into n sub-layers (n is an integer equal to or greater than two) and the j-th sub-layer of the n sub-layers is the specified layer (j is an integer, $1 \leq j \leq n$), "sub-layers in the vicinity of the specified sub-layer" represent the sub-layers located in front of and behind the j-th sub-layer, such as the (j+1)-th and (j−1)-th sub-layers and the (j+2)-th, (j+1)-th, (j−1)-th, and (j−2)-th sub-layers.

The less the number of sub-layers whose elemental composition ratio is corrected, the more efficiently the calculation to determine a composition depth profile can be performed. Therefore, from this standpoint, it is preferable to correct only elemental composition ratios for the specified sub-layer. However, considering an increase in calculation accuracy to some extent, it is also preferable to correct elemental composition ratios of the sub-layers in the vicinity of the specified sub-layer.

Further, as described above, it is preferable to keep a composition ratio corrected amount, which is used in correcting elemental composition ratios at least for the specified sub-layer so that the calculated intensities converge to the actually-measured intensities, constant or to decrease the composition ratio corrected amount in repeating the approximate calculation. Incidentally, the phrase "a composition ratio corrected amount" concretely means the sum of absolute values of relative density corrected amounts of the individual elements contained in the solid surface layer. The detailed description on the composition ratio corrected amount will be provided later.

The reason why to keep a composition ratio corrected amount constant or to decrease the composition ratio corrected amount in repeating the approximate calculation is preferable is as follows.

(1) Because the separation between a calculated composition depth profile and the true composition depth profile (which can be hereinafter referred to as "the profile separation width" for short) is large early in repeating the approximate calculation, a larger composition ratio corrected amount allows a calculated composition depth profile to converge to the true composition depth profile more effectively.

(2) In the case the separation between the calculated and true profiles has become smaller with an increase in the number of the repetition, however, it can become difficult to make the separation between calculated and true profiles smaller efficiently when the composition ratio corrected amount is excessively large.

Now, the phrase "to keep a composition ratio corrected amount constant in repeating the approximate calculation" represents that a composition ratio corrected amount in the (q+1)-th approximate calculation is the same as that of the q-th approximate calculation, where q is an integer equal to or greater than one.

When repeating the approximate calculation, whether to keep the composition ratio corrected amount constant or decrease the corrected amount in the approximate calculation with a certain repetition number must be determined from the viewpoint of reducing the profile separation width to a larger extent.

In contrast, as described above, between a composition ratio corrected amount and a profile separation width is a correlation such that a relatively larger composition ratio corrected amount with respect to the profile separation width can increase the profile separation width reversely instead of reducing it; a relatively smaller composition ratio corrected amount with respect to the profile separation width tends to reduce the profile separation width.

The profile separation width itself can be determined because the true composition depth profile is unknown. However, the profile separation width can be expressed indirectly using photoelectron intensities produced by an element contained in a solid surface layer at a certain density. Concretely, the profile separation width can be expressed as a difference between an actually-measured intensity and the calculated intensity, which can be hereinafter referred to as "a photoelectron intensity difference" for short.

Therefore, in the case where the difference between a photoelectron intensity difference when the composition ratio corrected amount is kept constant and a photoelectron intensity difference when an elemental composition ratio corrected amount is decreased, hereinafter referred to as "a calculated intensity converged amount with respect to the actually-measured intensity" for short, is relatively large, keeping the composition ratio corrected amount constant can make the profile separation width smaller.

Contrary, in the case where a calculated intensity converged amount with respect to the actually-measured intensity is relatively small, it is preferable to make the composition ratio corrected amount smaller. This is because the profile separation width can increase reversely instead of decreasing even when the composition ratio corrected amount is kept constant.

It is seen from the foregoing that the profile separation width tends to be saturated finally at a fixed value in the case where the approximate calculation is repeated while keeping the composition ratio corrected amount at a constant value in the situation in which the profile separation width is sufficiently large. This tendency represents that a decrease in the calculated intensity converged amount with respect to the actually-measured intensity tends to become smaller and thus the calculated intensity converged amount tends to converge to a fixed value as the number of repetition of the approximate calculation increases.

From this, it can be said that it is preferable to decrease the composition ratio corrected amount in the case where the variation of the calculated intensity converged amount with respect to the actually-measured intensity becomes smaller, or the calculated intensity converged amount substantially reaches a fixed value, as the approximate calculation is repeated.

The value of the calculated intensity converged amount with respect to the actually-measured intensity, which is used as a measure to judge whether to keep the composition ratio corrected amount constant or to decrease it, can be determined easily on the basis of experimental measurement information of a solid surface layer having an element composition similar to that of a solid surface to be measured.

In the case where this experimental measurement information has been accumulated sufficiently, it is preferable to utilize the information to make the setting such that the composition ratio corrected amount takes on a predetermined value at least in repeating the approximate calculation. In this case, it becomes unnecessary to judge whether or not to correct the elemental composition ratio each time the approximate calculation is repeated on the basis of a converged amount obtained each time the approximate calculation is repeated. As a result, the calculation to determine a composition depth profile can be performed more rapidly.

Embodiments

While embodiments of the invention will be described below, the invention is not limited to only such embodiments.

First, an embodiment of the invention will be described in general feature and qualitative actions of the individual constituent features.

More specifically, the analysis of a composition depth profile of a solid surface layer according to the invention is carried out at least utilizing an analyzing method composed of five steps, which includes a specified layer distinction step and an elemental composition ratio correcting step, as shown in FIG. 1.

FIG. 1 is a flow chart showing an embodiment of a method of analyzing a composition depth profile of a solid surface layer according to the invention. The method of analyzing a composition depth profile of a solid surface layer can be roughly broken down into five steps as follows: an initial value setting step; a precalculation step; a specified layer distinction step; an elemental composition ratio correcting step; and a calculation accuracy judging step. In addition, the four steps, namely the precalculation step, the specified layer distinction step, the elemental composition ratio correcting step, and the calculation accuracy judging step, constitute a loop algorithm. The loop algorithm is a section of performing the above-described approximate calculation. Repeating the loop algorithm, a composition depth profile of a solid surface layer can be obtained.

It is practically preferable to use the analyzing method including the five steps shown in FIG. 1 as a program for analyzing a composition depth profile of a solid surface layer written in a known programming language (e.g. Visual Basic, which allows the easy checking of changes in parameters during calculation).

However, it is noted that a method of analyzing a composition depth profile of a solid surface layer according to the invention (which can be hereinafter referred to as "an analyzing method of the invention" for short) is not limited to the arrangement shown in FIG. 1. The analyzing method of the invention is not limited particularly, as long as it includes at least the following two steps: a specified layer distinction step and an elemental composition ratio correcting step. Further, one or more other steps may be placed between, before, and/or after these steps, as required. Also, one or more other steps depending only on these steps, which correspond to subroutines in a computer program, may be prepared.

When analyzing a composition depth profile of a solid surface layer, the initial value setting step is carried out and then the loop algorithm is repeated once or more.

In the loop algorithm are carried out the precalculation step, the specified layer distinction step, the elemental composition ratio correcting step; and the calculation accuracy judging step in this order. In the time of carrying out the loop algorithm, if a desired calculation accuracy is not achieved in the calculation accuracy judging step, the program execution is returned back to the precalculation step again to carry out the steps in the loop algorithm from the beginning thereof in turn. If a desired calculation accuracy is achieved, the analysis program is terminated. Thus, an approximated composition ratio of elements in each of a plurality of sub-layers into which a solid surface layer has been temporarily divided, is obtained. In other words, a composition depth profile of the solid surface layer is provided.

The qualitative functions of the individual steps are as follows, but the concrete and detailed descriptions thereof will be presented later.

The initial value setting step is a step for providing various initial values (initial information other than numerical values, e.g., names of elements) required to perform the analysis process with the loop algorithm. The precalculation step is a step for previously calculating various parameters required at least in the specified layer distinction step and the elemental composition ratio correcting step. The specified layer distinction step is a step for distinguishing a layer such that calculated intensities converge best to the actually-measured intensities (a specified layer). The elemental composition ratio correcting step is a step for correcting elemental composition ratios at least for the specified layer so that calculated intensities converge to the actually-measured intensities, wherein the specified layer is one of a plurality of sub-layers into which a solid surface layer has been temporarily divided.

The calculation accuracy judging step is a step for comparing calculated intensities with the actually-measured intensities thereby to judge whether the difference between (1) a composition depth profile of a solid surface layer (hereinafter referred to as "an approximate profile" for short) obtained from the results of elemental composition ratios' correction in the elemental composition ratio correcting step, and (2) the actual composition depth profile (hereinafter referred to as "the true profile" for short) falls within a certain value range, i.e. whether a desired calculation accuracy is achieved.

In the case where the desired calculation accuracy is achieved in the calculation accuracy judging step, the program execution exits from the loop algorithm to terminate. Thus, an approximate profile is obtained. In the case where desired calculation accuracy is not achieved, the program execution is returned back to the beginning of the loop algorithm, i.e., the precalculation step, to repeat the process steps in the loop algorithm.

The invention has been described above without using any concrete mathematical expressions, etc. However, as long as the invention can be carried out utilizing parameters including at least actually-measured intensity values and calculated intensity values, one or more computational expressions, etc., the parameters and the expression or expressions, etc. are not limited particularly.

For example, the above-described approximate calculation (loop algorithm) is performed at least so as to cause calculated intensities to converge to the actually-measured intensities. However, in this case, the convergence judgement is not limited to a way to compare only calculated intensities and the actually-measured intensities, the judgement may be made by comparing calculated intensity ratios and the actually-measured intensity ratios. Further, for example, the convergence judgement may be made by judging whether or not the difference between calculated intensity ratios and the actually-measured intensity ratios approaches zero, etc.

Figure 4:
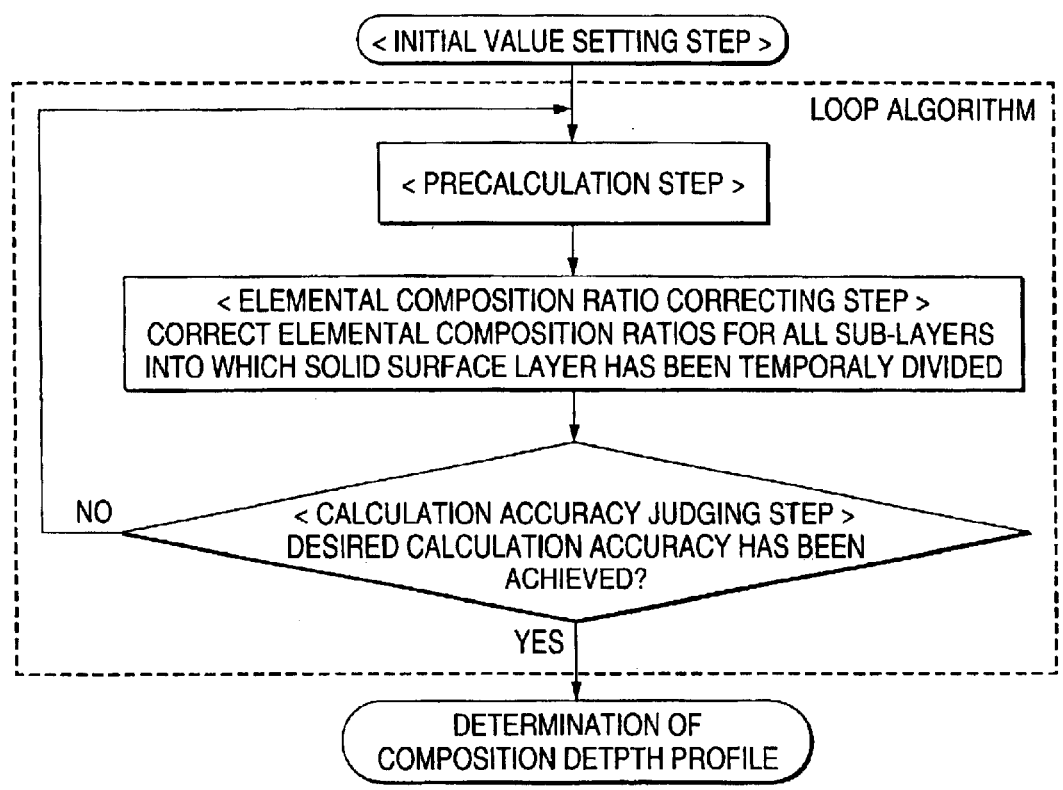
FIG. 4 is a flow chart showing a method of analyzing a composition depth profile of a solid surface layer in the related art.

Next, an embodiment of the invention will be described in contrast with a conventional method in the prior art. FIG. 4 is a flow chart showing a method of analyzing a composition depth profile of a solid surface layer in the prior art. The conventional method can be roughly broken down into four steps as follows: an initial value setting step, a precalculation step, an elemental composition ratio correcting step, and a calculation accuracy judging step. In addition, the three steps, namely the precalculation step, the elemental composition ratio correcting step, and the calculation accuracy judging step, constitute a loop algorithm. The loop algorithm is a section of performing the approximate calculation to determine an approximate profile. The loop algorithm is repeated once or more.

In the case of a method of analyzing a composition depth profile of a solid surface layer in the prior art (hereinafter referred to as a conventional analyzing method) shown in FIG. 4, the qualitative actions of the initial value setting step, the precalculation step, and the calculation accuracy judging step are basically the same as those of an analyzing method of the invention. The recalculation step is a step for previously calculating various parameters required at least in the elemental composition ratio correcting step.

As can be seen from FIGS. 1 and 4, the loop algorithm of the conventional analyzing method does not include the specified layer distinction step. Accordingly, in the elemental composition ratio correcting step, it has been basically required to correct elemental composition ratios so that calculated intensities converge to the actually-measured intensities for all sub-layers into which a solid surface layer has been temporarily divided.

In other words, the conventional analyzing method has required a lot of time to determine the density distributions of elements in a solid surface layer in the direction of the film thickness in the elemental composition ratio correcting step. This is because the conventional method is not a method such that the elemental composition ratios of one or more specified sub-layers selected in order to cause calculated intensities to converge to the actually-measured intensities effectively and efficiently are corrected, unlike an analyzing method of the invention.

Of course, the elemental composition ratio may not be corrected for all the sub-layers in the conventional analyzing method, too. However, the conventional analyzing method does not include a specified layer distinction step. For this reason, any sub-layers have no selection criteria to judge whether or not the correction of elemental composition ratios is required. Therefore, the sub-layers are merely treated as substantially equivalents. In other words, the judgement of whether to correct an elemental composition ratio for each of the sub-layers or not is not made selectively based on any judgement criterion but made by a process of trial and error. From this standpoint, it is possible to say that the case where the elemental composition ratio is not corrected for all the sub-layers and the case where elemental composition ratios for all the sub-layers are corrected are substantially equivalent.

In contrast, an analyzing method of the invention additionally includes a specified layer distinction step for the purpose of overcoming the drawbacks of the conventional analyzing method such that there is no selectivity for a layer whose elemental composition ratios are to be corrected in the elemental composition ratio correcting step. In the specified layer distinction step, the specified layer is distinguished to select the most suitable layer to correct an elemental composition ratio. Therefore, using the analyzing method of the invention to analyze a composition depth profile of a solid surface layer, the density distributions of elements in the solid surface layer in the direction of the film thickness can be determined simply and accurately for a short time.

The embodiment of the invention has been described above in general feature and qualitative actions of the individual constituent features. Next, the invention will be described in detail with reference to mathematical expressions, etc. so as to grasp the concrete calculation process in determining a composition depth profile of a solid surface layer.

As already described, the invention utilizes at least actually-measured intensities of photoelectrons emitted from a solid surface layer by irradiating the solid surface layer containing two or more species of elements with X rays and photoelectron calculated intensities obtained by making a calculation, wherein an elemental composition ratio is assumed for each of a plurality of sub-layers into which a solid surface layer has been temporarily divided, to determine a composition depth profile of the solid surface layer.

In this case, at least actually-measured intensities and calculated intensities corresponding to the actually-measured intensities are required. To obtain actually-measured intensities, it is preferable to use a method such that they can be measured as amounts of photoelectrons emitted when irradiating a solid surface with X rays, and more specifically the angle-resolved XPS. Accordingly, the following description is predicated on the case of using the angle-resolved XPS.

On the other hand, calculated intensities corresponding to the actually-measured intensities, which have been obtained by the measurement of a solid surface with the angle-resolved XPS, are determined according to the following procedure. First, a region of up to a certain depth from the solid surface, hereinafter referred to as "a solid surface layer," from which substantially detectable photoelectrons are emitted when irradiating the solid surface with X rays, is temporarily divided into a plurality of sub-layers. Second, the sum of intensities of photoelectrons emitted from the sub-layers is determined using a computational expression wherein the photoelectron attenuation principle expressed by the foregoing Equation (1) is utilized.

The calculated intensity corresponding to an actually-measured intensity is expressed by the sum of the intensities of photoelectrons emitted from each of sub-layers into which a solid surface layer has been temporarily divided. The expression to determine the calculated intensity has been determined by applying Equation (1) to a multilayer film model as shown in FIG. 2 concretely.

Figure 2:
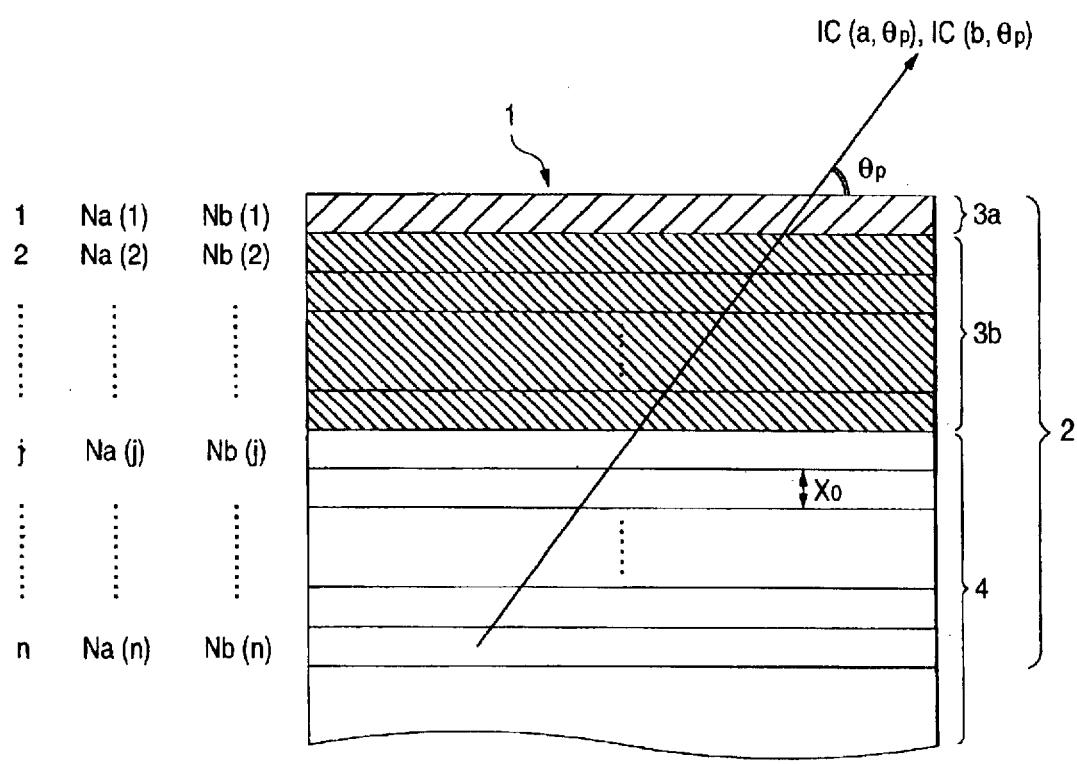
FIG. 2 is a conceptual drawing showing an example of multilayer film models used for the invention.

FIG. 2 is a conceptual drawing showing an example of the multilayer film model used in the invention. More concretely, FIG. 2 shows the case where a solid surface layer 2 having a certain thickness below the solid surface 1 is temporarily divided into n sub-layers with the thickness of $x_0$. The solid surface layer 2 in the multilayer film model is predicated on the condition of having a thickness equal to or less than about 10 nm, which permits photoelectrons to reach the solid surface 1 instead of disappearing during the XPS measurement. This approximation is made for the reason that ninety five percent of photoelectron intensities comes from photoelectrons created within a range from the solid surface 1 to a depth of $3\lambda \sin\theta$ and emitted therefrom during the actual measurement as can be seen from Equation (1), so that the information coming from a place deeper than the depth of $3\lambda \sin\theta$ can be treated as a substantially undetectable information.

The solid surface layer 2 is not limited particularly as long as it allows photoelectrons to be emitted therefrom when irradiating the solid surface 1 with X rays. Therefore, the solid surface layer 2 may be substantially the same as a bulk portion inside the solid, and a layer which includes an alteration layer different from the bulk portion in a region extending up to a certain depth below the solid surface, a thin film provided on the surface of a substrate, etc.

For example, when regarding the solid surface layer 2 as a gate nitride-oxide film of a semiconductor, the reference numerals 3a, 3b, and 4 can be regarded as indicating in turn from the solid surface 1 toward the inside of the solid a carbon (C) layer, a silicon nitride-oxide (SiON) layer, and a silicon substrate, respectively.

In FIG. 2, for example, when elements "a" and "b" are contained in the solid surface layer 2, the densities of the element "a" in the sub-layers are assumed to be $N_a(1)$, $N_a(2)$, ... $N_a(j)$, ... $N_a(n)$ in turn from the solid surface 1; the densities of the element "b" in the sub-layers are assumed to be $N_b(1)$, $N_b(2)$, ... $N_b(j)$, ... $N_b(n)$ in turn from the solid surface 1. Also, in the case where an element other than the elements "a" and "b" is contained in the solid surface layer 2, the densities thereof in the sub-layers are assumed similarly. In this case, the sums of intensities of photoelectrons, which are emitted from the first to n-th sub-layers at an angle of $\theta_p$ with respect to the solid surface 1 by launching X rays into the solid surface layer 2 at the angle of $\theta_p$ with respect to the surface thereof (not shown), are represented by $IC(a, \theta_p)$ for the element "a" and $IC(b, \theta_p)$ for the element "b." Also, in the case where an element other than the elements "a" and "b" is contained in the solid surface layer 2, the sum of emitted photoelectron intensities for the sub-layers is represented in the same way.

Therefore, assuming a multilayer film model as shown in FIG. 2, the sum of intensities $IC(a, \theta_p)$ of photoelectrons, which are produced by the element "a" and emitted from the first to n-th sub-layers at a photoelectron emission angle $\theta_p$, can be expressed as the following Equation (2). The description of a process to derive Equation (2) is omitted here, because the process does not concern the essence of the invention.

Equation (2) is expressed for the element "a." However, also in the case where other elements (e.g. elements indicated by the symbols: b, c, d, e, f, etc.) are contained in the solid surface layer 2, the equation can be applied to the other elements in the same manner as the element "a."

$$IC(a, \theta_p) = \delta_a k(\theta_p) \sum_{j=1}^{n} \left\{ N_a(j) \left[ 1 - \exp\left(\frac{x_0}{\lambda(j)\sin\theta_p}\right) \right] \prod_{k=1, j\geq 2}^{j-1} \exp\left(\frac{x_0}{\lambda(k)\sin\theta_p}\right) \right\} \quad (2)$$

where $N_a(j)$ is a relative density of the element "a" contained in the j-th sub-layer, $\delta_a$ is a photoelectron generative cross sectional area of the element "a", $k(\theta_p)$ is a device function, $\lambda(j)$ is an inelastic scattering mean free path of the element "a" in the case of assuming that the j-th sub-layer has a sufficient spatial expanse like a bulk, $\lambda(k)$ is an inelastic scattering mean free path of the element "a" in the case of assuming that the k-th sub-layer has a sufficient spatial expanse like a bulk, $x_0$ is a thickness of each sub-layer, $\theta_p$ is the p-th X ray incident angle, which is one of m levels' incident angles (an angle of a photoelectron detecting direction with respect to the solid surface 1) or an photoelectron emission angle (an angle of emitted photoelectrons with the solid surface 1), and i, j, k, m, n, and p each represent an integer equal to or greater than one. Incidentally, the photoelectron generative cross sectional area of the element "a", $\delta_a$ may be a value stated in a well-known literature cited, e.g., Kozo Tanaka et al., "X-sen Kodensi Bunkou-hou (X ray photoelectron spectroscopy)," pp.222–225, Maruzen Co. Ltd., 1998.

In the case where the multilayer film model shown in FIG. 2 is applied to the invention, it is desired in order to achieve the balance between an increase in calculation accuracy and a reduction in calculation time: to set the number of sub-layers n within a range of 2–100; and to set the thickness of each sub-layer $x_0$ within a range of 0.1–1 nm, and more preferably to set the thickness $x_0$ at a thickness equivalent to a unit atomic layer (about 2.7 Å).

In addition, $\lambda(k)$ may be well-known data (e.g. the data stated in the above literature by Kozo Tanaka et al., "X ray photoelectron spectroscopy," Maruzen Co. Ltd.). For example, in the case where the solid surface layer 2 temporarily divided into n sub-layers includes a C layer 3a, a SiON layer 3b, and a Si substrate 4 as illustrated in FIG. 2, the values which may be used as $\lambda(k)$ when the types of photoelectrons measured are $C_{1s}$, $O_{1s}$, $Si_{2p}$, $N_{1s}$ as listed in Table 1 are: the value in the column "λ in C" for photoelectrons going through the C layer 3a; the value in the column "λ in $SiO_2$" for photoelectrons going through the SiON layer 3b (the value in $SiO_2$ is used as an approximation of the value in SiON); and the value in the column "λ in Si" for photoelectrons going through the Si substrate 4.

TABLE 1

PHOTOELECTRON BINDING ENERGY Eb AND INELASTIC SCATTERING MEAN FREE PATH λ (Å) FOR EACH ELEMENT

| Element | Eb | λ in $SiO_2$ | λ in C | λ in Si |
|---|---|---|---|---|
| $O_{1s}$ | 503 | 28.2 | 26.0 | 23.5 |
| $Si_{2p}$ | 103 | 37.7 | 34.8 | 31.6 |
| $N_{1s}$ | 400 | 31.3 | 28.9 | 26.1 |
| $C_{1s}$ | 285 | 33.7 | 31.1 | 28.2 |

When referring to the specified elements contained in the solid surface layer 2 in the description below, the elements are expressed by lower-case alphabetic characters (e.g. a, b, c, d, etc.), or concrete symbols of elements (e.g. C, N, O, Si, etc). Therefore, for example, in the case of referring to the specified element contained in the solid surface layer 2, the left side of Equation (2) can be expressed as $IC(a, \theta_p)$, $IC(N, \theta_p)$, etc. In addition, the actually-measured intensity corresponding to a calculated intensity $IC(a, \theta_p)$ expressed using Equation (2) is herein expressed as $IR(a, \theta_p)$.

As described above, the invention utilizes Equation (2) derived by applying Equation (1) to the multilayer film model shown in FIG. 2 as a calculated intensity at a specified photoelectron emission angle produced by a particular element. However, the invention is not so limited. In the invention, another equation derived by applying another multilayer film model other than the above-described multilayer film model may be used, as long as a desired calculation accuracy can be achieved in determining a composition depth profile of the solid surface layer 2.

Next, another embodiment of an analyzing method of the invention, wherein calculated intensities expressed by Equation (2) described above are utilized, will be shown in FIG. 3.

Figure 3:
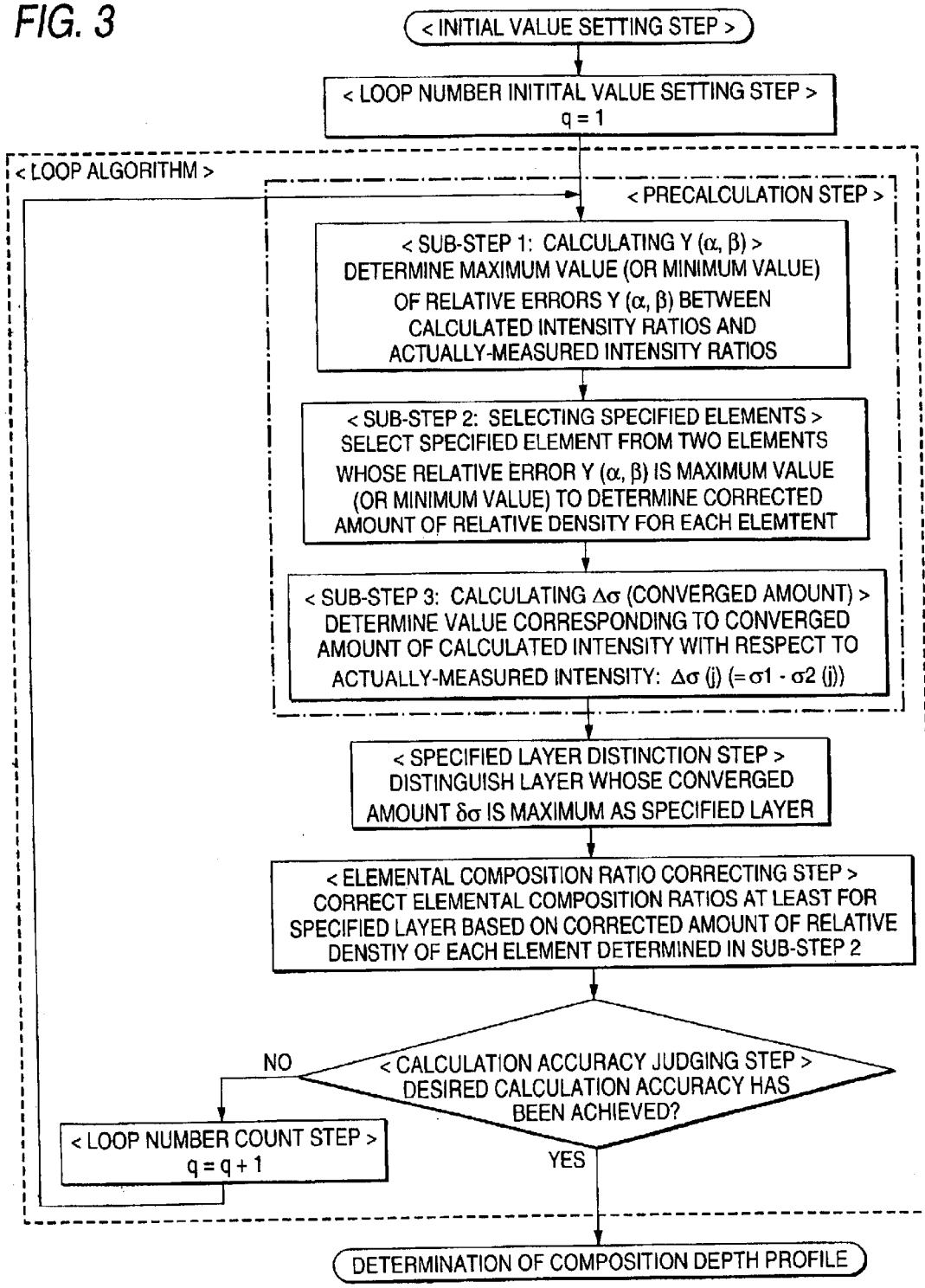
FIG. 3 is a flow chart showing another embodiment of a method of analyzing a composition depth profile of a solid surface layer according to the invention.

FIG. 3 is another exemplary flow chart showing a method of analyzing a composition depth profile of a solid surface layer of the invention. In other words, FIG. 3 shows an exemplary flow chart in the case where calculated intensities expressed by Equation (2) are utilized in the embodiment shown in FIG. 1.

The basic arrangement of the flow chart shown in FIG. 3 and basic actions of the individual steps are in common with the case of the flowchart shown in FIG. 1, which has been already described. However, in the flow chart shown in FIG. 3, the precalculation step is composed of three sub-steps, namely a sub-step 1, a sub-step 2, and a sub-step 3; the sub-steps are carried out in this order. The sub-steps will be described in detail later.

In addition, the analyzing method of the invention includes a loop number initial value setting step in order to count the number of repetitions of the loop algorithm between the initial value setting step and the precalculation step. The analyzing method further includes a loop number count step in order to count the number of repetitions of the loop algorithm on its way back to the precalculation step (sub-step 1) when a desired calculation accuracy is not achieved in the calculation accuracy judging step. The individual steps shown in the flow chart of FIG. 3 will be described in detail below.

The initial value setting step is a step for providing various initial values required to perform the analysis process, with the loop algorithm (initial information other than numerical values including the names of elements). Concretely, the initial values are: <1> constituent elements and the elemental composition ratio thereof in the individual sub-layers (values for the first calculation), which are used to calculate a calculated intensity $IC(a, \theta_p)$ using Equation (2) in the precalculation step; <2> actually-measured intensities $IR(a, \theta_p)$ at each angle for each element, which is determined by using the angle resolved XPS to measure a solid surface layer actually; and <3> other initial values including various parameters and constants other than the values stated in <1> and <2>, which are required to carry out an analyzing method of the invention.

A prerequisite for carrying out an analyzing method of the invention is that the constituent elements of the solid surface layer have been known. Further, in the case where the elemental composition ratio of the solid surface layer, the construction and film thicknesses of layers constituting the solid surface layer, etc. other than the constituent elements of the solid surface layer have been grasped to a certain degree, it is also desirable to utilize those information as other initial values for increasing the accuracy of the calculation process and reducing the calculation time. These initial values can be easily obtained by analyzing the solid surface layer using XPS or other analyzing methods.

$IR(a, \theta_p)$, an actually-measured intensity at the angle $\theta_p$ for the element "a" can be determined by using the angle resolved XPS to measure a solid surface layer. However, the analyzing conditions involved in carrying out the program shown in FIG. 1, e.g., the measurement range of $\theta_p$, the number of levels for incident angles m, and an angular interval between the adjacent levels $\Delta\theta_p$, are not limited particularly as long as they are within the scope of what an XPS apparatus used for the measurement of actually-measured intensities $IR(a, \theta_p)$ can cope with.

However, from the practical viewpoints of increasing the calculation accuracy, reducing the calculation time, and reducing the measurement time required by the XPS apparatus, etc., it is desired to set the analyzing conditions as follows. The measurement range of $\theta_p$ is set between 5 and 90 degrees. The number of the $\theta_p$ levels m is set at a number equal to or greater than n+1 (n is the number of sub-layers into which a solid surface layer has been temporarily divided). The angular interval $\Delta\theta_p$ is set between 1 and 15 degrees.

The sub-step 1 is a step for determining a relative error Y(a,b) used to select specified elements in the sub-step 2 and a population (relative errors Y(a,b)) used to determine a standard deviation σ1 utilized in the sub-step 3.

The relative error Y(a,b) is a value acquire by subtracting a calculated intensity ratio of two different elements "a" and "b" from the actually-measured intensity ratio thereof and dividing the resultant difference by the actually-measured intensity ratio. Concretely, the relative error Y(a,b) is expressed by the following equation:

$$Y(a, b) = \frac{1}{m}\sum_{p=1}^{m} \frac{(IR(a, \theta_p)/IR(b, \theta_p)) - (IC(a, \theta_p)/IC(b, \theta_p))}{(IR(a, \theta_p)/IR(b, \theta_p))} \quad (3)$$

where $\theta_p$ is the p-th photoelectron emission angle, which is one of m levels' photoelectron emission angles, $IR(a, \theta_p)$ is an actually-measured intensity at a photoelectron emission angle $\theta_p$ for the element "a", $IR(b, \theta_p)$ is an actually-measured intensity at a photoelectron emission angle $\theta_p$ for the element "b", IC(a, $\theta_p$) is a calculated intensity at a photoelectron emission angle $\theta_p$ for the element "a", IC(b, $\theta_p$) is a calculated intensity at a photoelectron emission angle $\theta_p$ for the element "b", "a" and "b" are different elements contained in the solid surface layer, p and m are integers equal to or greater than one.

As already described, the invention includes distinguishing a specified layer such that a calculated intensity converge best to the actually-measured intensity and repeating the approximate calculation for correcting elemental composition ratios at least for the specified layer so as to cause a calculated intensity to converge to the actually-measured intensity thereby to determine a composition depth profile of the solid surface layer. In this step, it is required to compare a calculated intensity with the actually-measured intensity thereby to check the extent to which the calculated intensity converges to the actually-measured intensity.

However, there are m combinations of calculated intensities and actually-measured intensities for each of the elements contained in a solid surface layer, where m is the number of levels of the angle $\theta_p$. Therefore, even in the case where elemental composition ratios of the individual sub-layers are assumed to be constant, it can be difficult to compare calculated intensities with the actually-measured intensities for all the combinations thereof and grasp the extent to which calculated intensities convert to the actually-measured intensities by simply comparing calculated intensities with the actually-measured intensities. In addition, actually-measured intensity values, which have been obtained by the measurement, include the components of variations coming from the measurement to a greater or lesser degree. For this reason, simply comparing calculated intensities with the actually-measured intensities to grasp the extent to which calculated intensities converge to the actually-measured intensities can make the calculation accuracy lower consequently.

In this case, it is preferable to take averages of calculated and actually-measured intensities over the number of all the levels of the angle $\theta_p$ in order to overcome the former problem. Further, in order to overcome the latter problem, it is preferable to take photoelectron intensity ratios produced by two elements, i.e. an actually-measured intensity ratio and a calculated intensity ratio, and to adopt a relative error obtained by dividing the difference between a calculated intensity (or calculated intensity ratio) and the actually-measured intensity (or actually-measured intensity ratio) by the actually-measured intensity (or actually-measured intensity ratio). Equation (3) presented above is intended to enable the comparison between a calculated intensity and the actually-measured intensity in consideration of the foregoing.

Incidentally, all the combinations for two elements selected from the elements contained in the solid surface layer may be adopted as the combination of the elements "a" and "b" in Equation (3). However, the combination of the elements "a" and "b" in Equation (3) may not be so limited, as long as at least the combinations on which all the constituent elements of the solid surface layer are reflected without any omissions are adopted.

More specifically, in the case where C, Si, O, and N are contained in a solid surface layer temporarily divided into n sub-layers as illustrated in FIG. 2, examples of the combinations of the elements "a" and "b" (a, b) include (C, Si), (C, O), (C, N), (Si, O), (N, Si), and (N, O), provided that the left side elements inside the parentheses correspond to the numerators of the individual intensity ratios shown in Equation (3); the right side elements inside the parentheses correspond to the denominators of the individual intensity ratios.

Therefore, the values which can be taken as a relative error Y(a,b) in this case are: Y(C,Si), Y(C,O), Y(C,N), Y(Si,O), Y(N,Si), and Y(N,O) corresponding to the number of combinations of two elements, namely six.

Incidentally, the invention will be hereinafter described, assuming an example where four elements, C, Si, O, and N are contained.

As described above, in the sub-step 1, a Y value, which is the maximum (or minimum) in the six Y values, is distinguished; a population required to determine the standard deviation σ1 used in the sub-step 3, namely a set of the above six Y values, is determined.

The sub-step 2 includes selecting one or both of two elements associated with a Y value, which is the maximum (or minimum) in the six Y values determined in the sub-step 1, as the specified element. The sub-step 2 also includes determining composition ratio corrected amounts used in the case of temporarily changing elemental composition ratios of the individual sub-layers in the sub-step 3 described later, and determining a composition ratio corrected amount used in the case of correcting elemental composition ratios at least for the specified sub-layer in the elemental composition ratio correcting step.

Incidentally, in the invention, "temporarily changing elemental composition ratios" means that the results of changing the elemental composition ratios are not reflected on an approximate profile, namely a result of the calculation in the elemental composition ratio correcting step; "correcting an elemental composition ratio" means that the result of changing the elemental composition ratio is reflected on an approximate profile, namely a result of the calculation in the elemental composition ratio correcting step.

The corrections of elemental composition ratios are performed in order to cause an approximate profile obtained by repeating the loop algorithm to converge to a true profile to the greatest extent practicable finally. However, when comparing approximate profiles and the true profiles, approximate profiles and the true profiles rarely deviate from each other for all of the four elements (C, Si, O, and N) contained in the solid surface layer equivalently. In many cases, any of the four elements deviate relatively significantly; the remaining elements don't deviate to a large extent, relatively.

In such cases, correcting relative densities of all the elements with the same value (e.g., −3% for C, −3% for O, +3% for Si, and +3% for N) causes an approximate profile of a certain element to converge to the true profile better, but it not only cannot cause an approximate profile of the other element to converge to the true profile, but also reversely can make the separation therebetween larger. Considering all the elements, there can be the case where approximate profiles do not converge to the true profiles eventually and totally.

Therefore, correcting the relative density of an element with a large relative deviation width by a large amount and correcting the relative density of an element with a small relative deviation width by a small amount, it becomes possible to cause approximate profiles to converge to the true profiles more efficiently.

When those corrections are conducted, an element with a large relative deviation width, namely a specified element, may be distinguished to set the absolute value of a relative density corrected amount for the element larger than the other elements. Further, in this case, one or both of two elements associated with a Y value, which is the maximum in the six Y values, can be selected as the specified element.

This is because a Y value indirectly expresses a separation width between an approximate profile and the true profile in connection with two elements using calculated intensities and the actually-measured intensities, also as can be seen from the above description and Equation (3).

Accordingly, for example, when the Y(C,Si) is the maximum in the six Y values, C and/or Si can be selected as the specified element. For example, in the case where a composition ratio corrected amount, which represents the sum of absolute values of relative density corrected amounts of the individual elements, has been 12% in the elemental composition ratio correcting step of the immediately preceding loop, when C and Si are selected as specified elements, relative density corrected amounts of the four elements may be, for example, as follows: −5% for C, −1% for O, +5% for Si, and +1% for N. In this case, the absolute values of corrected amounts of C and Si, which are specified elements, can be relatively larger than those of the other two elements.

While one or both of two elements associated with a Y value, which is the maximum in the six Y values, can be selected as the specified element, in order to perform the approximate calculation more efficiently, it is preferable to select one specified element when the number of species of elements contained in the solid surface layer is small. In addition, when the number of species of the elements is large, it is preferable to select two specified elements.

As in the case of selecting the specified element based on a maximum Y value, it is also possible to select the specified element based on a minimum Y value. In the invention, however, it is preferable to select the specified element based on a Y value having a larger absolute value of maximum and minimum Y values.

Further, in the case where a Y value used as a basis in selecting the specified element concerns the elements "a" and "b", i.e., the case where the Y(a,b) is used as the basis, it is preferable to determine an increase and a decrease in relative density corrected amount for a specified element such that the corrected amount of the element "a" is increased (the corrected amount of the element "b" is decreased) when Y(a,b)>0, or the corrected amount of the element "a" is decreased (the corrected amount of the element "b" is increased) when Y(a,b)<0.

On the other hand, as already described, in the case where the composition ratio corrected amount applied in the elemental composition ratio correcting step of the immediately preceding loop is excessively large, it becomes only difficult to effectively reduce the separation between an approximate profile and the true profile, and the separation therebetween can become larger reversely. In such case, it is preferable to reduce the composition ratio corrected amount. In the foregoing example, relative density corrected amounts of the four elements in the case of correcting the composition ratio corrected amount from 12% to 6% may be, for example, as follows: −2.5% for C, −0.5% for O, +2.5% for Si, and +0.5% for N.

Whether to keep the composition ratio corrected amount constant or decrease the corrected amount, concretely whether to keep the composition ratio corrected amount 12% or decrease the corrected amount from 12% to 6%, can be determined by trial and error. However, it is preferable to determine what to do about the composition ratio corrected amount on the basis of the change in calculated intensity converged amount with respect to the actually-measured intensity, which has been determined in the approximate calculation in the immediately preceding loop or the loop before then, more specifically on the basis of the change in difference $\Delta\sigma(j)$ between a standard deviation $\sigma1$ and a standard deviation $\sigma2(j)$, which is described later.

Concretely, the case where the calculated intensity converged amount with respect to the actually-measured intensity hardly changes with the repetition of the approximate calculation and the calculated amount has shown substantially a constant value during such repetition means that the separation between the approximate profile and the true profile has not been reduced. Therefore, in this case, it is preferable to decrease the composition ratio corrected amount.

Further, as already described, the composition ratio corrected amount in repeating the approximate calculation may be predetermined on the basis of experimental measurement information. For example, the composition ratio corrected amount may be made one half every a certain number of times of repetition of the approximate calculation depending on the number of times the approximate calculation is repeated.

As described above, in the sub-step 2, it is possible to select the specified element and to set a composition ratio corrected amount depending on the separation width between an approximate profile of each element contained in the solid surface layer and the true profile so as to cause the approximate profile to converge to the true profile most effectively.

Referring now to the sub-step 3, wherein the variable $\sigma2(j)$ is a standard deviation of six Y values obtained in the case of temporarily changing only an elemental composition ratio of the j-th sub-layer in n sub-layers into which a solid surface layer has been temporarily divided using the composition ratio corrected amount determined in the sub-step 2. The sub-step 3 is a step for calculating a difference between a standard deviation of the six Y values $\sigma1$ determined in the sub-step 1 and a standard deviation the $\sigma2(j)$, namely $\Delta\sigma(j)$ [$=\sigma1-\sigma2(j)$].

Incidentally, the magnitude of $\Delta\sigma(j)$ indirectly represents an amount of change in separation width between an approximate profile, in which an elemental composition ratio of the j-th sub-layer has been corrected, and the true profile. More specifically, $\Delta\sigma(j)$ corresponds to a calculated intensity converged amount with respect to the actually-measured intensity, which has been described. This is because $\Delta\sigma(j)$ is expressed by $\sigma1-\sigma2(j)$ and the standard deviations $\sigma1$ and further $\sigma2(j)$ is expressed using Equation (3).

The specified layer distinction step is a step for distinguishing a sub-layer (a specified sub-layer) such that a calculated intensity is caused to converge best to the actually-measured intensity. In an analyzing method of the invention shown in FIG. 3, a layer whose converged amount $\Delta\sigma(j)$ is the maximum in calculated intensity converged amounts $\Delta\sigma(j)$ Is with respect to the actually-measured intensities for the individual sub-layers determined in the sub-step 3 is distinguished as a specified sub-layer.

The elemental composition ratio correcting step is a step for correcting elemental composition ratios at least for the specified sub-layer in n sub-layers into which a solid surface layer has been temporarily divided such that calculated intensities converge to the actually-measured intensities. The step is carried out by correcting elemental composition ratios at least for a sub-layer (a specified sub-layer) whose converged amount $\Delta\sigma(j)$ is the maximum in the n sub-layers, in an analyzing method of the invention shown in FIG. 3.

The correction of an elemental composition ratio is performed on the basis of the results determined in the sub-step 2 (a composition ratio corrected amount and relative density corrected amounts of the individual elements).

In the calculation accuracy judging step in the embodiment shown in FIG. 3, a parameter which indirectly represents the separation width between an approximate profile and the true profile is used to judge whether or not a desired calculation accuracy has been achieved. The parameter indirectly representing the separation width between an approximate profile and the true profile is not limited particularly. However, for example, the maximum value in values of the relative errors Y's determined in the sub-step 1 may be used as the parameter.

In this case, when the reference value to judge whether or not a desired calculation accuracy has been achieved is the maximum value in values of the relative errors Y's, the reference value can be set freely while keeping a good balance between a desired calculation accuracy and the calculation time. However, it is preferable to set the reference value within a range from about 1% to 2% from a practical standpoint.

In the case where a desired calculation accuracy has been achieved, an exit from the loop algorithm occurs to terminate the program and thus an approximate profile can be obtained. In the case where a desired calculation accuracy has not been achieved yet, the program execution is again returned back to the precalculation step located at the beginning of the loop algorithm to repeat the process in the loop algorithm.

Next, a preferred application of the invention described above will be described. The analyzing method of the invention is not limited particularly in the applications thereof, as long as the analyzing method is applied to a solid surface capable of emitting photoelectrons when irradiating the solid surface with X rays. However, the analyzing method is significantly suitable for analyzing composition depth profiles for thin films of a nitride-oxide material and a high dielectric material, e.g., $HfO_2$ and $Al_2O_3$, such as a gate insulating film of a semiconductor device.

It is preferable to utilize the analyzing method of the invention in the form of a program written in a known programming language in order to facilitate the calculation processing. In addition, it is especially preferable to utilize the analyzing method of the invention in the form of a program written in Visual Basic, which allows the easy checking of the calculation process particularly.

As described above, the invention can provide a method of analyzing a composition depth profile of a solid surface layer, wherein the addition of a selectivity for causing photoelectron calculated intensities to converge to the actually-measured intensities effectively and efficiently allows the simple and accurate determination of the density distributions of elements in a solid surface layer in the direction of the film thickness for a short time.

What is claimed is:

1. A method of analyzing a composition depth profile of a solid surface layer, wherein actually-measured intensity of photoelectrons emitted from said solid surface layer by irradiating said solid surface layer containing at least two or more species of element with X rays and photoelectron calculated intensity obtained by making a calculation assuming an elemental composition ratio for each of a plurality of sub-layers into which said solid surface layer has been temporarily divided are utilized to determine a composition depth profile of said solid surface layer, the method comprising a step of at least repeating an approximate calculation including:

distinguishing a specified sub-layer such that the calculated intensity best converges to the actually-measured intensity in said sub-layers; and correcting an elemental composition ratio at least for said specified sub-layer so that the calculated intensity converges to the actually-measured intensities, thereby determining the composition depth profile of said solid surface layer.

2. The method of analyzing a composition depth profile of a solid surface layer of claim 1, an elemental composition ratio only for said specified sub-layer is corrected so that the calculated intensity converges to the actually-measured intensity.

3. The method of analyzing a composition depth profile of a solid surface layer of claim 1, wherein a composition ratio corrected amount, which is used in correcting an elemental composition ratio at least for said specified sub-layer so that the calculated intensity converges to the actually-measured intensity, is kept constant or decreased in repeating said approximate calculation.

4. The method of analyzing a composition depth profile of a solid surface layer of claim 2, wherein a composition ratio corrected amount, which is used in correcting an elemental composition ratio at least for said specified sub-layer so that the calculated intensity converges to the actually-measured intensity, is kept constant or decreased in repeating said approximate calculation.

5. The method of analyzing a composition depth profile of a solid surface layer of claim 3, wherein the composition ratio corrected amount is decreased in the case where a fluctuation of convergence in calculated intensity with respect to the actually-measured intensity has become smaller in repeating said approximate calculation.

6. The method of analyzing a composition depth profile of a solid surface layer of claim 3, wherein the composition ratio corrected amount takes a predetermined value at least in repeating said approximate calculation.

7. The method of analyzing a composition depth profile of a solid surface layer of claim 1, wherein said solid surface layer comprises at least a nitride-oxide material.

8. The method of analyzing a composition depth profile of a solid surface layer of claim 2, wherein said solid surface layer comprises at least a nitride-oxide material.

9. The method of analyzing a composition depth profile of a solid surface layer of claim 1, wherein said solid surface layer comprises at least a high dielectric material.

10. The method of analyzing a composition depth profile of a solid surface layer of claim 2, wherein said solid surface layer comprises at least a high dielectric material.

11. The method of analyzing a composition depth profile of a solid surface layer of claim 9, wherein said high dielectric material comprises at least $HfO_2$ or $Al_2O_3$.

12. The method of analyzing a composition depth profile of a solid surface layer of claim 10, wherein said high dielectric material comprises at least $HfO_2$ or $Al_2O_3$.

13. The method of analyzing a composition depth profile of a solid surface layer of claim 1, wherein said approximate calculation is carried out by at least a program written in Visual Basic.

14. The method of analyzing a composition depth profile of a solid surface layer of claim 2, wherein at least said approximate calculation is carried out by at least a program written in Visual Basic.

* * * * *